United States Patent
Nakagawa et al.

(10) Patent No.: US 9,063,343 B2
(45) Date of Patent: Jun. 23, 2015

(54) IMAGE PROCESSING APPARATUS, INCUBATION OBSERVING APPARATUS, AND IMAGE PROCESSING METHOD

(75) Inventors: Masato Nakagawa, Kyoto (JP); Hirotada Watanabe, Yokohama (JP); Yoichi Wada, Kawasaki (JP)

(73) Assignees: NIKON CORPORATION, Tokyo (JP); KYOTO UNIVERSITY, Kyoto (JP)

( * ) Notice: Subject to any disclaimer, the term of this patent is extended or adjusted under 35 U.S.C. 154(b) by 355 days.

(21) Appl. No.: 13/351,666

(22) Filed: Jan. 17, 2012

(65) Prior Publication Data
US 2012/0114219 A1   May 10, 2012

Related U.S. Application Data

(63) Continuation of application No. PCT/JP2010/004652, filed on Jul. 20, 2010.

(30) Foreign Application Priority Data

Jul. 21, 2009   (JP) ................................. 2009-170160

(51) Int. Cl.
| | |
|---|---|
| G06K 9/00 | (2006.01) |
| G02B 21/36 | (2006.01) |
| C12M 1/00 | (2006.01) |
| C12M 1/34 | (2006.01) |
| C12M 1/36 | (2006.01) |
| G02B 21/14 | (2006.01) |

(52) U.S. Cl.
CPC .............. *G02B 21/367* (2013.01); *C12M 41/14* (2013.01); *C12M 41/36* (2013.01); *C12M 41/48* (2013.01); *G02B 21/14* (2013.01)

(58) Field of Classification Search
None
See application file for complete search history.

(56) References Cited

U.S. PATENT DOCUMENTS

| | | | |
|---|---|---|---|
| 5,687,251 A | * 11/1997 | Erler et al. | ..................... 382/133 |
| 7,933,435 B2 | * 4/2011 | Hunter et al. | ................. 382/128 |
| 7,979,212 B2 | * 7/2011 | Gholap et al. | .................. 702/19 |

(Continued)

FOREIGN PATENT DOCUMENTS

| | | |
|---|---|---|
| EP | 2 202 291 A1 | 6/2010 |
| JP | A-2007-20422 | 2/2007 |
| JP | A-2007-155982 | 6/2007 |
| JP | A-2009-89629 | 4/2009 |
| WO | WO 2006/092925 A1 | 9/2006 |
| WO | WO 2007/069666 A1 | 6/2007 |
| WO | WO 2009/031283 A1 | 3/2009 |
| WO | WO 2009/057831 A1 | 5/2009 |

OTHER PUBLICATIONS

International Preliminary Report on Patentability issued in International Patent Application No. PCT/JP2010/004652 dated Jan. 24, 2012 (with translation).
Okita, Keisuke et al., "Generation of germline-competent induced pluripotent stem cells," Nature, 2007, vol. 448, pp. 313-318.
International Search Report issued in International Patent Application No. PCT/JP2010/004652 dated Sep. 7, 2010.

*Primary Examiner* — Jon Chang
*Assistant Examiner* — Oneal R Mistry
(74) *Attorney, Agent, or Firm* — Oliff PLC

(57) ABSTRACT

An image processing apparatus includes an outline extracting processing unit inputting a phase contrast image of a cell colony acquired by an observing unit, and extracting an outline of the cell colony, an extracting unit extracting a feature quantity of an outline part of the cell colony based on brightness information at an outside and brightness information at an inside of the outline on the phase contrast image, and an automatic discriminating unit automatically discriminating whether or not the cell colony is an iPS cell colony based on a discriminant criterion determined in advance and the feature quantity extracted by the extracting unit.

13 Claims, 12 Drawing Sheets

(56) References Cited

U.S. PATENT DOCUMENTS

| | | |
|---|---|---|
| 8,019,143 B2 * | 9/2011 | Kanda .......................... 382/133 |
| 8,417,011 B2 * | 4/2013 | Klottrup et al. .............. 382/133 |
| 2002/0106119 A1 * | 8/2002 | Foran et al. .................. 382/133 |
| 2005/0002552 A1 * | 1/2005 | Dunn et al. .................. 382/133 |
| 2005/0136509 A1 * | 6/2005 | Gholap et al. ................ 435/40.5 |
| 2006/0039593 A1 * | 2/2006 | Sammak et al. .............. 382/133 |
| 2008/0279441 A1 * | 11/2008 | Matsuo et al. ................ 382/133 |
| 2009/0047263 A1 * | 2/2009 | Yamanaka et al. ......... 424/93.21 |
| 2009/0141960 A1 * | 6/2009 | Yamamoto .................... 382/133 |
| 2010/0074507 A1 * | 3/2010 | Klottrup et al. .............. 382/133 |
| 2011/0013821 A1 * | 1/2011 | Mimura et al. .............. 382/133 |

* cited by examiner

Fig. 12
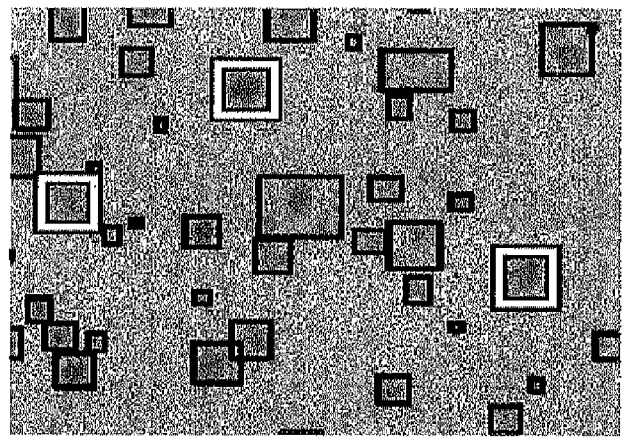
Fig. 13A  Fig. 13B
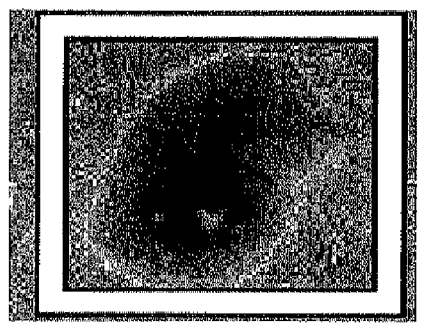 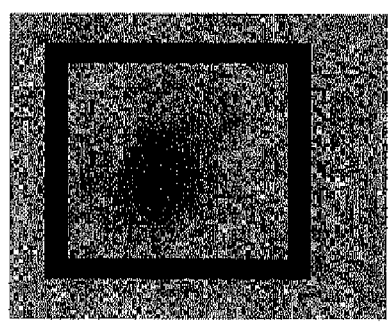
Fig. 14
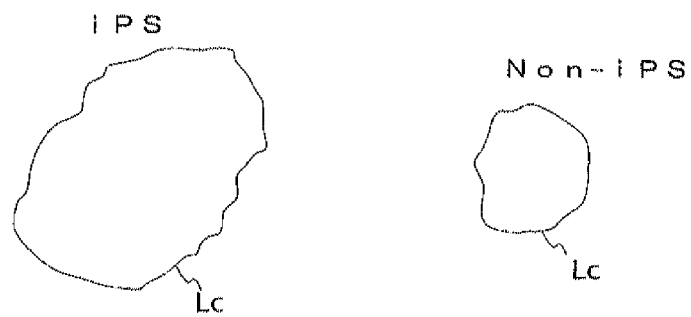

IMAGE PROCESSING APPARATUS, INCUBATION OBSERVING APPARATUS, AND IMAGE PROCESSING METHOD

CROSS REFERENCE TO RELATED APPLICATION

This application is a continuation application of International Application No. PCT/JP2010/004652, filed on Jul. 20, 2010, designating the U.S., in which the International Application claims a priority date of Jul. 21, 2009, based on prior filed Japanese Patent Application No. 2009-170160, the entire contents of which are incorporated herein by reference.

BACKGROUND

1. Field

The present application relates to an incubation observing apparatus observing a culturing state of an iPS cell colony, an image processing apparatus and an image processing method applied thereto when differentiated somatic cells are initialized to generate induced pluripotent stem cells (cells having pluripotency and proliferation potency near ES cells, and hereinafter it is referred to as "iPS cells").

2. Description of the Related Art

Conventionally, when iPS cells derived from mouse are generated, a mouse in which fluorescent protein gene (EGFP gene) is inserted into a locus of ECAT4 (Nanog) recognized as a pluripotency-maintaining genes is used to visualize presence/absence of initialization of cells. In this case, the EGFP becomes an initialization marker, and it is possible to verify whether or not the cells are initialized by presence/absence of fluorescence (refer to Non-Patent Document 1: Keisuke Okita, Tomoko Ichisaka, and Shinya Yamanaka, "Generation of germline-competent induced pluripotent stem cells", Nature Vol 448, 19 Jul. 2007, P313-317, and so on).

However, a usage of a marker gene should be avoided when iPS cells derived from human are generated for a usage of regenerative medicine.

A proposition of the present application is to provide an image processing apparatus, an incubation observing apparatus, and an image processing method capable of discriminating presence/absence of initialization of cells without using a marker gene such as a fluorescent protein gene.

SUMMARY

An image processing apparatus includes an outline extracting processing unit inputting a phase contrast image of a cell colony acquired by an observing unit, and extracting an outline of the cell colony, an extracting unit extracting a feature quantity of an outline part of the cell colony based on brightness information at an outside and brightness information at an inside of the outline on the phase contrast image, and an automatic discriminating unit automatically discriminating whether or not the cell colony is an iPS cell colony based on a discriminant criterion determined in advance and the feature quantity extracted by the extracting unit.

An incubation observing apparatus includes a temperature-controlled room housing an incubation container, an imaging unit acquiring a phase contrast image of the incubation container housed in the temperature-controlled room, and the image processing apparatus processing the phase contrast image acquired by the imaging unit.

An image processing method includes an outline extracting processing step inputting a phase contrast image of a cell colony acquired by an observing unit, and extracting an outline of the cell colony, an extracting step extracting a feature quantity of an outline part of the cell colony based on brightness information at an outside and brightness information at an inside of the outline on the phase contrast image, and an automatic discriminating step automatically discriminating whether or not the cell colony is an iPS cell colony based on a discriminant criterion determined in advance and the feature quantity extracted at the extracting step.

The image processing apparatus, the incubation observing apparatus, and the image processing method capable of discriminating presence/absence of initialization of cells without using a marker gene such as a fluorescent protein gene are enabled.

BRIEF DESCRIPTION OF THE DRAWINGS

FIG. 12 is a partial enlarged view of the composite macro image I (an appearance when a frame of a designated cell colony is changed.).

FIG. 13A is an enlarged view of a designated cell colony, and FIG. 13B is an enlarged view of a cell colony which is not designated.

FIG. 14 is examples of outline Lc.

DETAILED DESCRIPTION OF THE EMBODIMENTS

[First Embodiment]

Hereinafter, a first embodiment of the present invention is described. The present embodiment is an embodiment of an incubator.

At first, a structure of an incubator according to the present embodiment is described.

Figure 1:
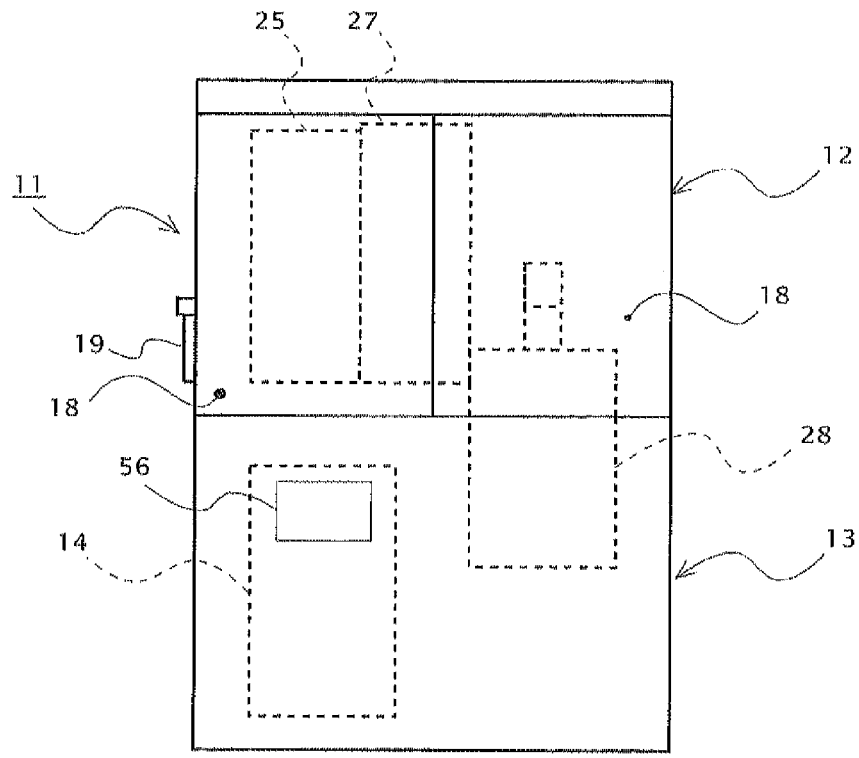
FIG. 1 is a front view of an incubator.
Figure 2:
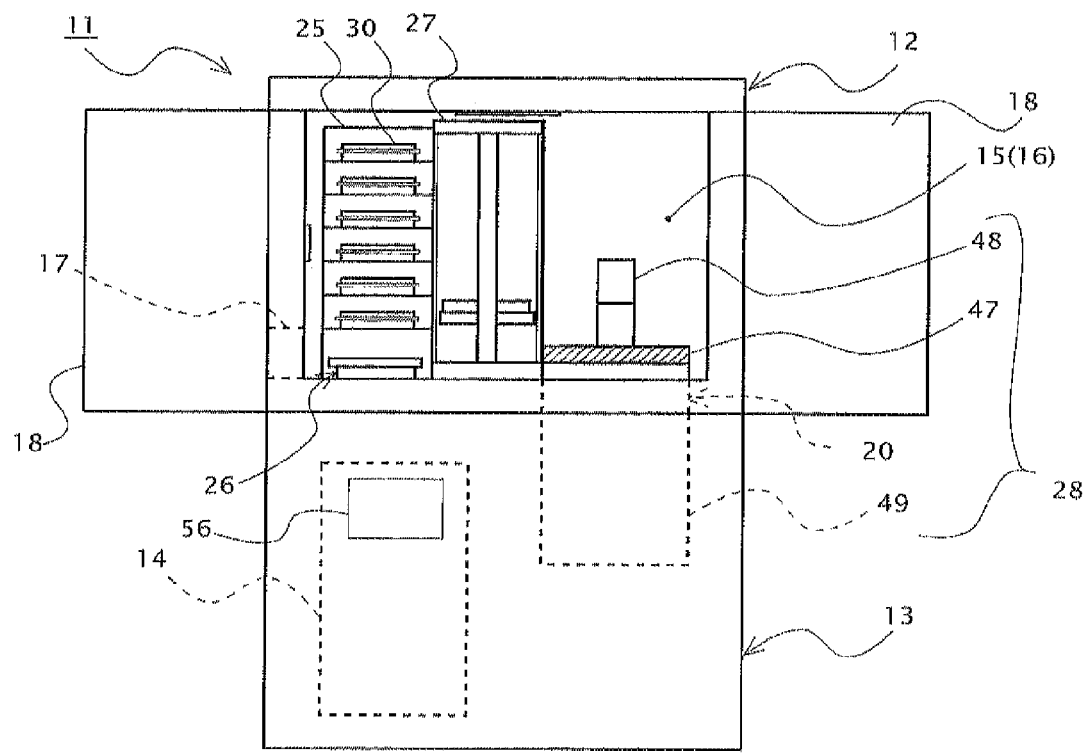
FIG. 2 is a front view of the incubator when a front door 18 is opened.

FIG. 1 is a front view of an incubator according to the present embodiment, and FIG. 2 is a front view of the incubator when a front door 18 is opened. As illustrated in FIG. 1 and FIG. 2, an incubator 11 includes a first housing 12 performing incubation of living cells, and a second housing 13 housing a controlling unit 14. The first housing 12 is disposed at an upper part of the second housing 13.

An operation panel 56 is provided at a front surface of the second housing 13, and a monitor, an input button, and so on are provided at the operation panel 56. The controlling unit 14 and a part of an observing unit 28 are disposed inside the second housing 13.

A temperature-controlled room 15 (FIG. 2) covered with a heat insulating material is formed inside the first housing 12. This temperature-controlled room 15 is connected with outside via a front aperture 16 (FIG. 2) formed at a front of the first housing 12 and a carry-in entrance 17 (FIG. 2) formed at a left side surface of the first housing 12. Between them, the front aperture 16 (FIG. 2) is openable/closable by the front door 18 with hinged double doors, and the carry-in entrance 17 (FIG. 2) is openable/closable by a sliding automatic door 19 (FIG. 1). Note that a size of the carry-in entrance 17 is set to be a size in which an incubation container 30 (FIG. 2) is able to pass through. Besides, an aperture 20 (FIG. 2) is formed at a bottom surface of the first housing 12 at a right-of-center position when it is seen from a front side, and a part of the observing unit 28 is projectingly provided from the aperture 20 (FIG. 2).

A temperature adjuster, an atomizer, a gas introducing part, an environment sensor unit, and so on are housed at a wall surface of the temperature-controlled room 15. Among them, the temperature adjuster has a Peltier element, and heating or cooling of the temperature-controlled room 15 (FIG. 2) is performed by a Peltier effect. The atomizer adjusts humidity inside the temperature-controlled room 15 (FIG. 2) by atomizing inside the temperature-controlled room 15 (FIG. 2). The gas introducing part is coupled to a carbon dioxide cylinder at an outside of the incubator, and adjusts a carbon dioxide concentration inside the temperature-controlled room 15 (FIG. 2) by introducing carbon dioxide from the carbon dioxide cylinder to the temperature-controlled room (FIG. 2). The environment sensor unit detects each of the temperature, the humidity, and the carbon dioxide concentration inside the temperature-controlled room 15 (FIG. 2).

A container 25, a container carry in/out mechanism 26 (FIG. 2), and a container transfer mechanism 27 are disposed inside the first housing 12, and a part of the observing unit 28 is also disposed as stated above.

A disposed position of the container 25 is at a left side of the temperature-controlled room 15 (FIG. 2) when it is seen from the front of the first housing 12. The container 25 includes plural shelves, and the incubation containers 30 can be housed in respective shelves. A lowermost of the container 25 continues to the carry-in entrance 17 (FIG. 2) of the first housing 12, and the container carry in/out mechanism 26 (FIG. 2) to carry in/out the incubation container 30 is provided at the lowermost space.

A disposed position of the container transfer mechanism 27 is a center of the temperature-controlled room 15 (FIG. 2) when it is seen from the front of the first housing 12. The container transfer mechanism 27 performs a transfer of the incubation container 30 (FIG. 2) among the container 25, the container carry in/out mechanism 26 (FIG. 2), and the observing unit 28.

A disposed position of the observing unit 28 is at a right side of the temperature-controlled room 15 (FIG. 2) when it is seen from the front of the first housing 12. The observing unit 28 includes a sample stage 47 (FIG. 2), an arm 48 (FIG. 2) projecting at an upward of the sample stage 47 (FIG. 2), and a main body part 49 (FIG. 2). Among them, the sample stage 47 (FIG. 2) and the arm 48 (FIG. 2) position at the temperature-controlled room 15 (FIG. 2) side of the first housing 12, and the main body part 49 (FIG. 2) positions at the second housing 13 side.

Figure 3:
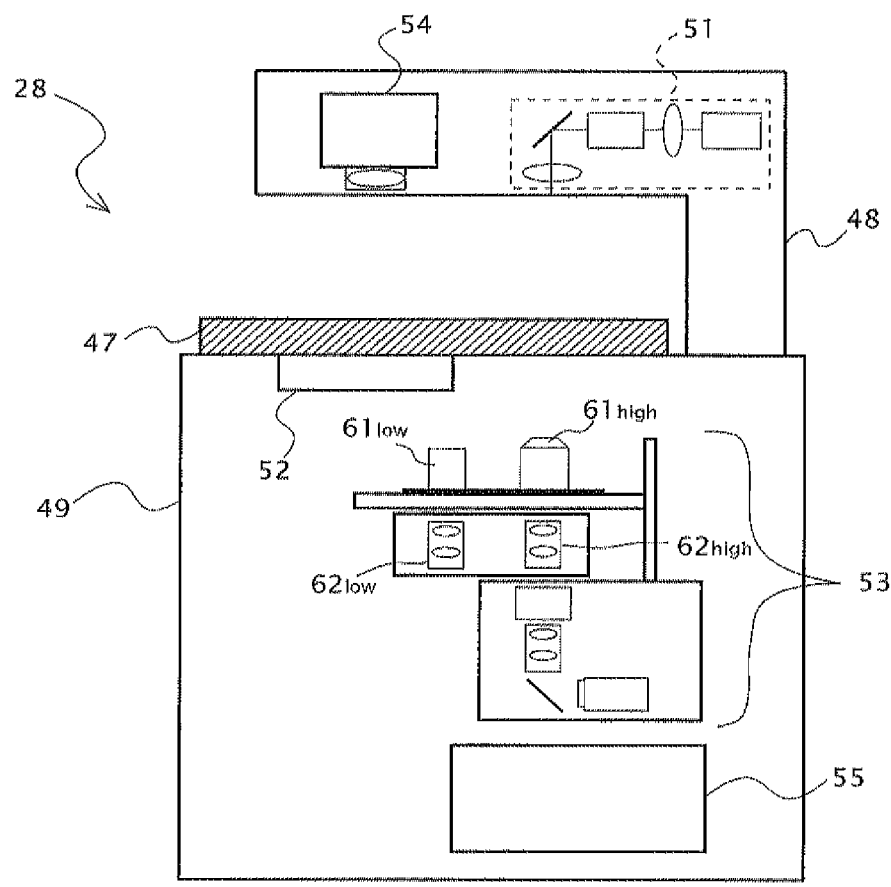
FIG. 3 is a schematic diagram illustrating a configuration of an observing unit 28.

FIG. 3 is a schematic diagram illustrating a configuration of the observing unit 28. As illustrated in FIG. 3, the observing unit 28 includes the sample stage 47, a first illumination part 51, a second illumination part 52, a microscopic observing part 53, a container observing part 54, and an image processing part 55.

Among them, the microscopic observing part 53 is housed in the main body part 49, and the first illumination part 51 is disposed at a position facing the microscopic observing part 53 of the arm 48. The microscopic observing part 53 and the fist illumination part 51 make up a microscope for phase contrast observation.

Besides, the container observing part 54 is housed in the arm 48, and the second illumination part 52 is disposed at a position facing the container observing part 54 of the main body part 49. The container observing part 54 and the second illumination part 52 make up an observing system for reflecting observation.

The sample stage 47 is made up of a translucent material, and the incubation container 30 is placed thereon. The sample stage 47 is made up of a high-accuracy stage, and it is possible to insert the incubation container 30 into an optical path of the microscope for phase contrast observation (the microscopic observing part 53 and the first illumination part 51) and into an optical path of the observing system for reflecting observation (the container observing part 54 and the second illumination part 52) by moving the incubation container 30 in a horizontal direction (XY direction).

Besides, the sample stage 47 is able to perform focusing of the microscope for phase contrast observation by changing a positional relationship between the incubation container 30 and the microscope for phase contrast observation in a Z direction. Besides, the sample stage 47 is able to change an observing point of the microscope for phase contrast observation by changing a positional relationship between the incubation container 30 and the microscope for phase contrast observation in the XY direction.

The observing unit 28 is able to capture an image of a reflected image of a whole of the incubation container 30 under a state in which the incubation container 30 is inserted into the optical path of the observing system for reflecting observation (the container observing part 54 and the second illumination part 52). Hereinafter, an image acquired by this imaging is referred to as a "reflected image".

Besides, the observing unit 28 is able to capture an image of a partial magnified phase contrast image of the incubation container 30 under a state in which the incubation container 30 is inserted into the optical path of the microscope for phase contrast observation (the microscopic observing part 53 and the first illumination part 51). Hereinafter, an image acquired by the imaging is referred to as a "phase contrast image".

Note that a combination of an objective lens 61 and a phase filter 62 of the microscopic observing part 53 is able to switch among plural kinds of combinations of which observation magnifications are different. For example, it can be switched between a combination for double observation (the objective lens 61 of low and the phase filter 62 of low) and a combination for quad observation (the objective lens 61 of high and the phase filter 62 of high).

Accordingly, the observing unit 28 is able to acquire a phase contrast image of double magnification (low-magnified phase contrast image) under a state in which the objective lens 61 of low and the phase filter 62 of low are set at the optical path, and to acquire a phase contrast image of quad magnification (high-magnified phase contrast image) under a state in which the objective lens 61 of high and the phase filter 62 of high are set at the optical path.

The image processing part 55 performs various image processing for an image (any of the reflected image, the low-magnified phase contrast image, or the high-magnified phase contrast image) acquired by the observing unit 28. Note that there are colony detecting processing (described later) and so on detecting a cell colony from an image in the image processing capable of being executed by the image processing part 55.

Next, an electrical system of the incubator 11 is described.

Figure 4:
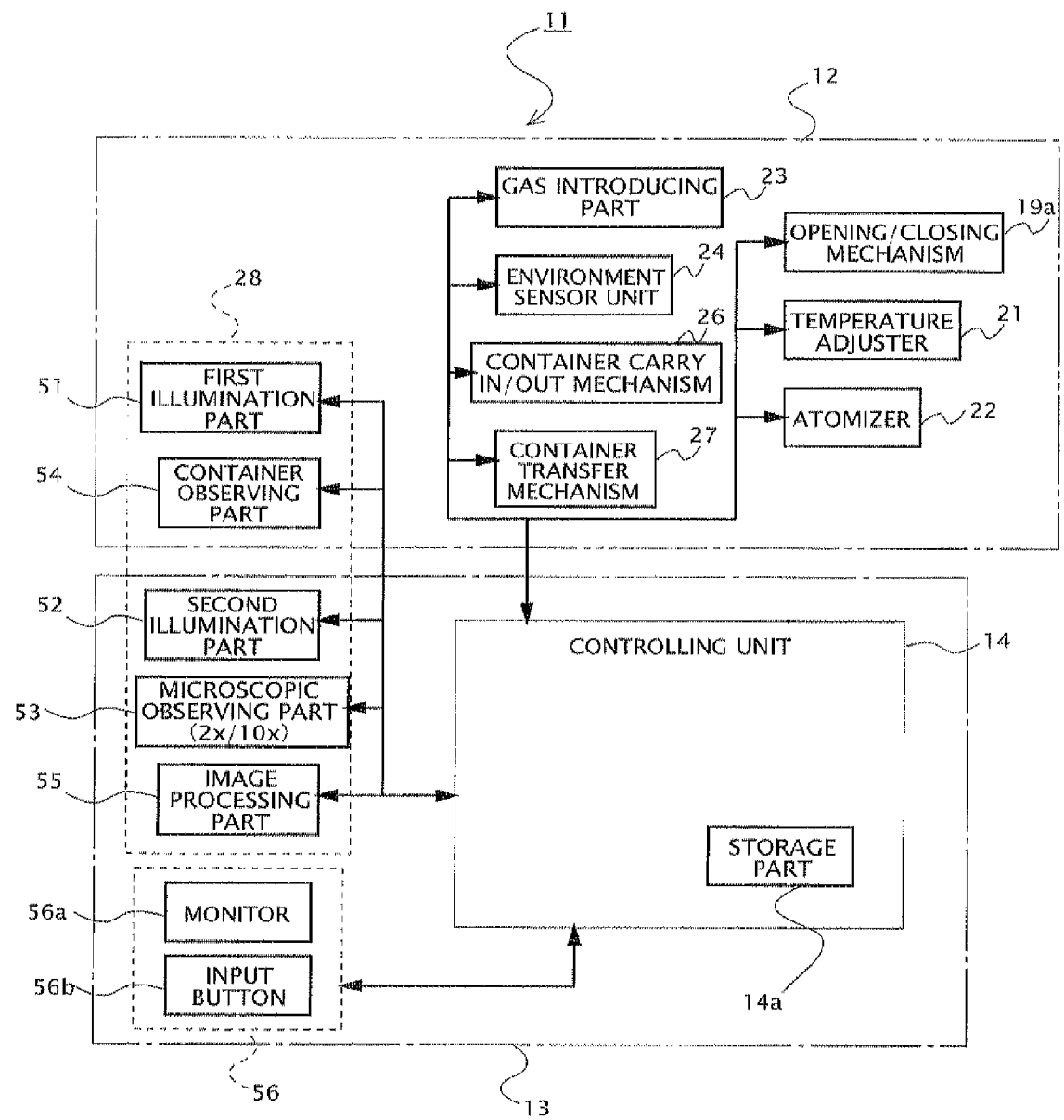
FIG. 4 is a circuit block diagram of an incubator 11.

FIG. 4 is a circuit block diagram of the incubator 11. As illustrated in FIG. 4, the controlling unit 14 of the incubator 11 is coupled to each of a door opening/closing mechanism 19a of the automatic door 19, a temperature adjuster 21, an atomizer 22, a gas introducing part 23, an environment sensor unit 24, the container carry in/out mechanism 26, the container transfer mechanism 27, the observing unit 28, a monitor 56a, and an input button 56b.

The controlling unit 14 totally controls each part of the incubator 11 in accordance with predetermined control programs. As an example, the controlling unit 14 maintains inside the temperature-controlled room 15 to be a predetermined environmental condition by controlling each of the temperature adjuster 21, the atomizer 22, the gas introducing part 23, and the environment sensor unit 24. Besides, the controlling unit 14 controls the observing unit 28 and the container transfer mechanism 27 to automatically execute an observation sequence of the incubation container 30 based on an observing schedule input by an user.

Besides, the controlling unit 14 includes a storage part 14a made up of a hard disk, a nonvolatile memory, and so on, to store various data such as observing data, management data, learning image number data, learning sample data, and discriminant plane data. Among them, the observing data are data prepared by each incubation container, the management data are data prepared by each experiment, and the learning image number data and the learning sample data are data common to all experiments. Note that operation programs necessary for operation of the controlling unit 14 are also stored at the storage part 14a, and the later-described operation of the controlling unit 14 follows to the operation programs.

Next, the incubation container 30 according to the present embodiment is described.

The incubation container 30 is a petri dish (dish), and a feeder cell layer is formed at a bottom part thereof. A dedicated culture medium layer where plural human somatic cells grow up is provided on the feeder cell layer, and a gene necessary for acquiring pluripotency is introduced into each of the human somatic cells beforehand. After a certain period (for example, for a week) has passed from an incubation start time, a part of the human somatic cells growing up in the incubation container 30 becomes iPS cells to form an iPS cell colony.

Normally, plural pieces (here, 50 pieces) of incubation containers 30 are simultaneously incubated in one experiment. There is a case when kinds of genes introduced into cells are different from one another among the 50 pieces of incubation containers 30, and an appearance ratio of the iPS cell colony is various. Accordingly, an observing schedule of these 50 pieces of incubation containers 30 is set to count the appearance ratio of the iPS cell colony by each container after it is incubated for approximately one week. The experiments with the observing schedule as stated above are normally performed for several times while exchanging incubation container groups being incubation objects.

Next, the operation of the controlling unit 14 in each experiment is described.

Figure 5:
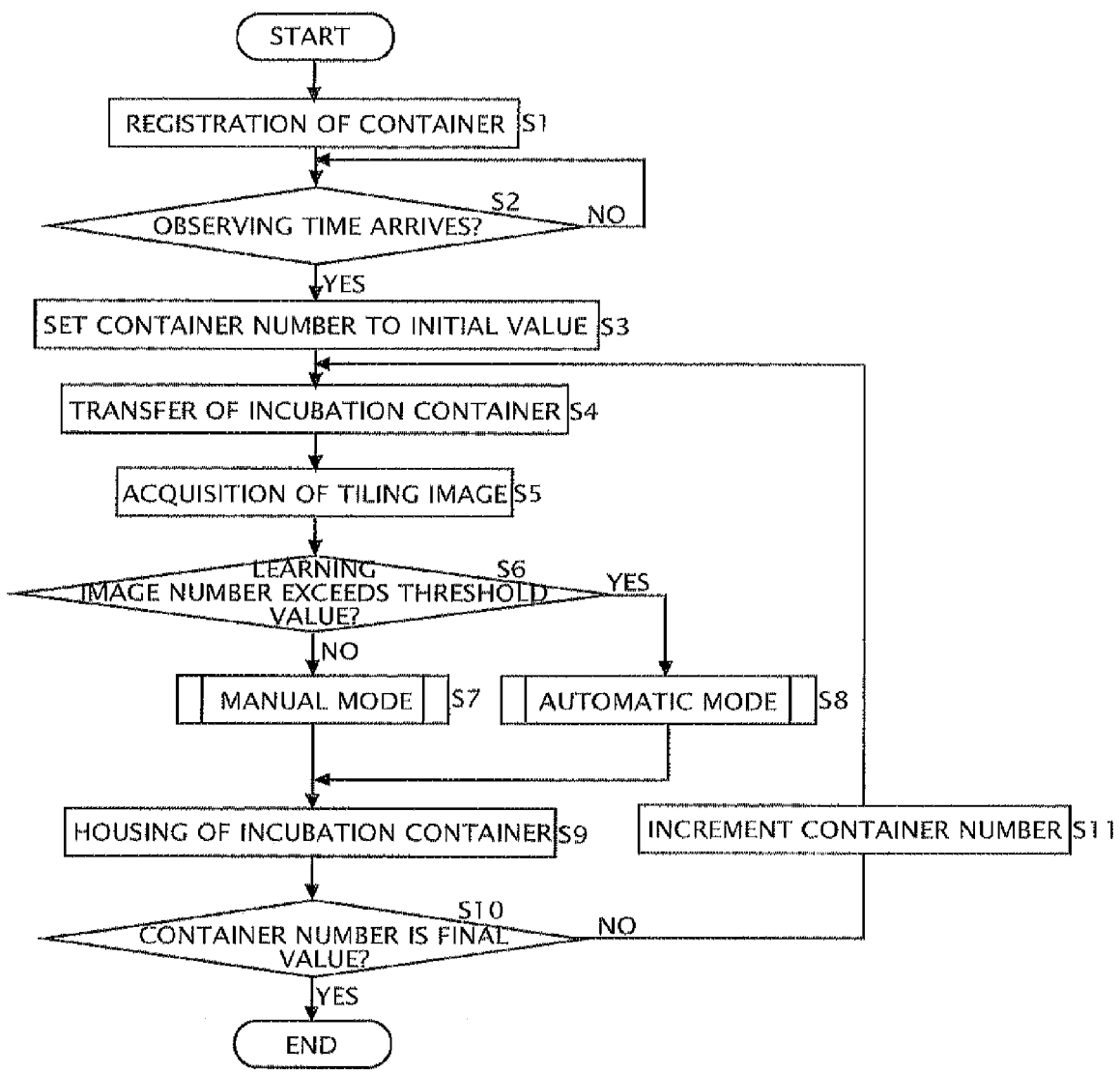
FIG. 5 is an operation flowchart of a controlling unit 14 in each experiment.

FIG. 5 is an operation flowchart of the controlling unit 14 in each experiment. Hereinafter, each step is described in sequence.

Step S1: The controlling unit 14 performs registrations of the 50 pieces of incubation containers 30 by, for example, the following processes (1) to (6).

(1) The controlling unit 14 carries in the incubation container 30 inserted to the carry-in entrance 17 by the user into the temperature-controlled room 15, and instructs the container transfer mechanism 27 to transfer the incubation container 30. The container transfer mechanism 27 transfers the incubation container 30 to place at a predetermined position of the sample stand 47.

(2) The controlling unit 14 instructs the observing unit 28 to acquire the reflected image of the incubation container 30. The observing unit 28 disposes the incubation container 30 at the optical path of the observing system for reflecting observation (the container observing part 54 and the second illumination part 52), acquires the reflected image of the incubation container 30 under the state, then displays the image on the monitor 56a, and writes to the observing data.

(3) The controlling unit 14 instructs the container transfer mechanism 27 to house the incubation container 30 to the container 25. The container transfer mechanism 27 houses the incubation container 30 to the container 25.

(4) The controlling unit 14 registers all of the 50 pieces of the incubation containers 30 by repeating the processes of (1) to (3) for 50 times. Note that the controlling unit 14 assigns container numbers 1 to 50 for the 50 pieces of incubation containers 30 registered at one time in a registration sequence.

(5) The controlling unit 14 lets the user input an observing schedule (incubation condition, incubation period, observation contents, and so on) relating to the registered 50 pieces of incubation containers 30. Here, it is assumed that the observing schedule to count the appearance ratio of the iPS cell colony by each container after the incubation is performed for approximately one week is input by the user. Note that an information input from the user to the controlling unit 14 is performed via the input button 56b (it is the same in the following process.). The controlling unit 14 writes the observing schedule input by the user to the management data of the experiment of this time.

(6) The controlling unit 14 starts the incubation of the registered 50 pieces of incubation containers 30 in accordance with the observing schedule written to the management data of the experiment of this time.

Step S2: The controlling unit 14 compares the observing schedule written to the management data of the experiment of this time with a current date and hour, and discriminates whether or not an observing time of the incubation container 30 arrives. When the observing time arrives, the process transfers to step S3, and when the observing time does not arrive, the process waits.

Step S3: The controlling unit 14 sets the container number to an initial value.

Step S4: The controlling unit 14 instructs the container transfer mechanism 27 to transfer the incubation container 30 corresponding to the current container number (hereinafter, called as a "focused incubation container 30"). The container transfer mechanism 27 carries out the focused incubation container 30 from the container 25 to place at the predetermined position of the sample stage 47.

Figure 8:
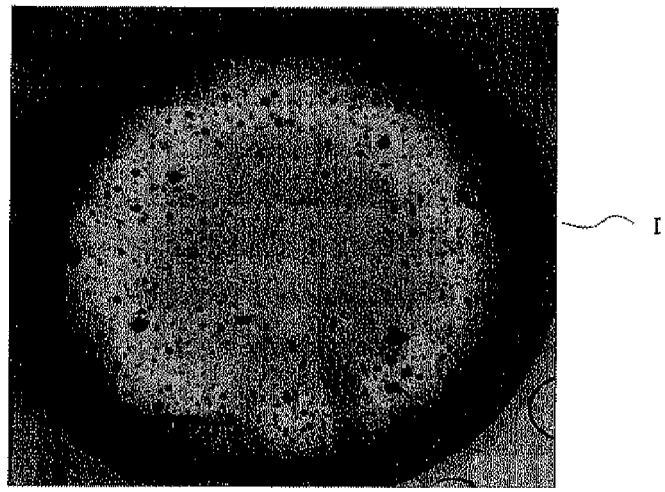
FIG. 8 is an example of a composite macro image I.

Step S5: The controlling unit 14 instructs the observing unit 28 to acquire the high-magnified phase contrast image of the whole of the focused incubation container 30. The observing unit 28 disposes the focused incubation container 30 at the optical path of the microscope for phase contrast observation (the microscopic observing part 53 and the first illumination part 51), and sets the combination of the objective lens 61 and the phase filter 62 to be the combination for quad observation (the objective lens $61_{high}$ and the phase filter $62_{high}$), and repeatedly acquires the high-magnified phase contrast images while shifting observing points in a step state under the above-stated state. Further, the observing unit 28 acquires the high-magnified phase contrast image of the whole of the focused incubation container 30 (composite macro image I) by tiling (connecting) the acquired plural high-magnified phase contrast images. Further, the controlling unit 14 writes the composite macro image I to the observing data of the focused incubation container 30, and displays on the monitor 56a (refer to FIG. 8).

Step S6: The controlling unit 14 compares the learning image number data at a current time with a threshold value (for example, 50 pieces), then the process transfers to a manual mode (step S7) when it does not exceed the threshold value, and transfers to an automatic mode (step S8) when it exceeds the threshold value. Note that the manual mode (step S7) is a mode in which the user performs a manual discrimination (teaching) of the iPS cell colony, and the controlling unit 14 learns the result. Besides, the automatic mode (step S8) is a mode in which the controlling unit 14 performs an automatic discrimination of the iPS cell colony. Besides, the learning image number data at the current time means the total number of images used for learning up to the current time.

Step S9: The controlling unit 14 instructs the container transfer mechanism 27 to house the focused incubation container 30 to the container 25. The container transfer mechanism 27 houses the focused incubation container 30 to the container 25.

Step S10: The controlling unit 14 discriminates whether or not the container number reaches a final value (here, 50), and the process transfers to step S11 when it does not reach the final value, and the flow is finished when it reaches the final value.

Step S11: The controlling unit 14 increments the container number, and then the process returns to the step S4.

Next, the operation of the controlling unit 14 in the manual mode is described.

Figure 6:
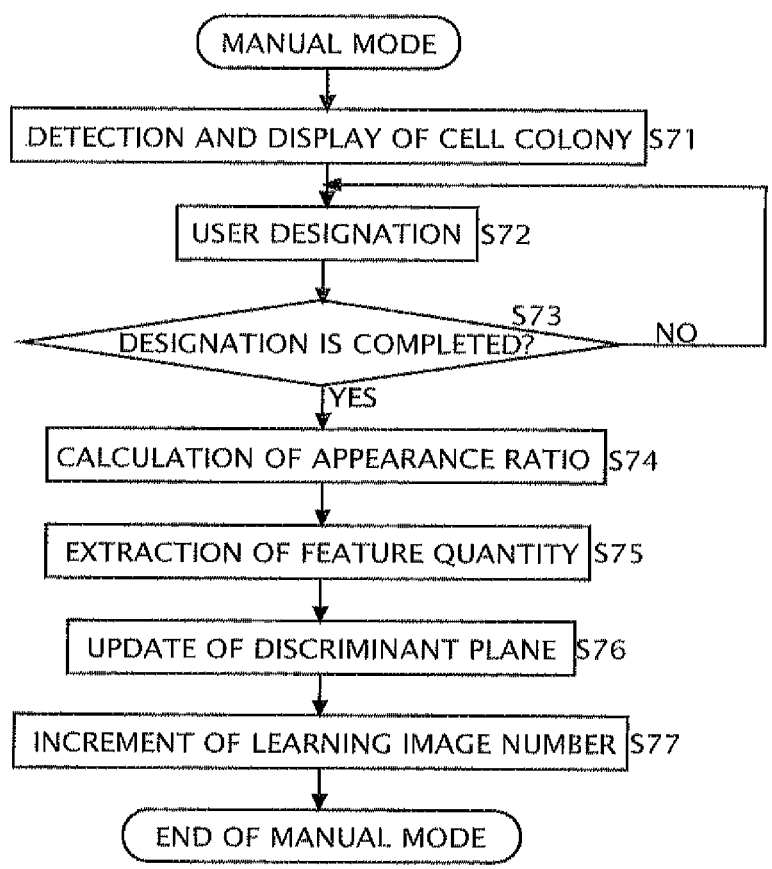
FIG. 6 is an operation flowchart of the controlling unit 14 in a manual mode.

FIG. 6 is an operation flowchart of the controlling unit 14 in the manual mode. Hereinafter, each step is described in sequence.

Figure 9:
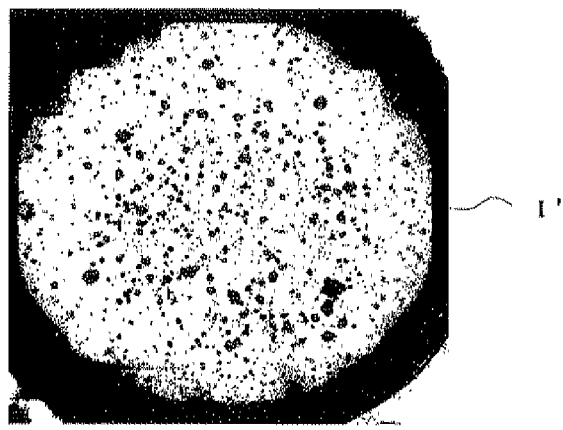
FIG. 9 is an example of a binarized image I'.
Figure 10:
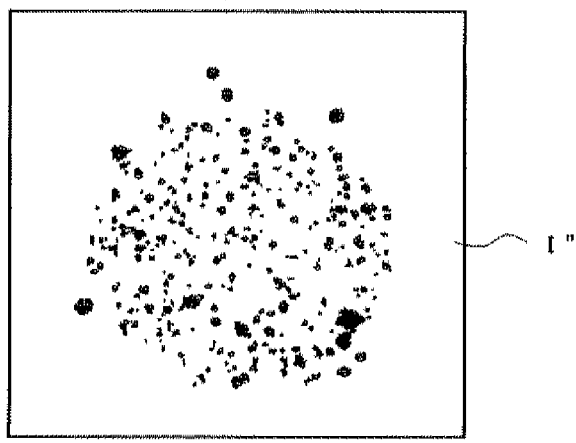
FIG. 10 is an example of a binarized colony image I".
Figure 11:
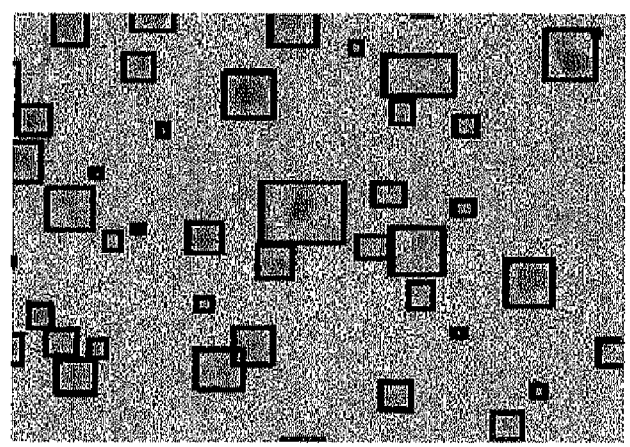
FIG. 11 is a partial enlarged view of the composite macro image I.

Step S71: The controlling unit 14 provides the composite macro image I (FIG. 8) of the focused incubation container 30 to the image processing part 55, and instructs the image processing part 55 to perform the colony detecting processing. The image processing part 55 acquires a binarized image (FIG. 9) by performing binarizing processing for the composite macro image I, and acquires a binarized colony image I" (FIG. 10) by excluding dark areas of which area size is out of a predetermined range from among plural dark areas appeared at the binarized image I'. The image processing part 55 outputs the binarized colony image I" to the controlling unit 14 as a detection result. The controlling unit 14 regards each of the plural dark areas appeared at the banarized colony image I" as cell colonies, creates rectangular frame images (frame image) surrounding each of the cell colonies, and overlaps the frame images on the composite macro image I displayed on the monitor 56a (FIG. 11).

Step S72: The controlling unit 14 instructs the user to designate the in cell colony on the displayed composite macro image I. Note that an information output from the controlling unit 14 to the user is performed via the monitor 56a (it is the same in the following process.). The user finds the iPS cell colony from among the plural cell colonies displayed on the monitor 56a, and designates the iPS cell colony to the controlling unit 14. The controlling unit 14 visualizes the designated contents by the user (FIG. 12) by changing a state (for example, color, thickness, line type, and so on) of the rectangular frame surrounding the cell colony when the cell colony is designated. Note that when the Non-iPS cell colony is designated by mistake, the user releases the designation by designating the cell colony again. The controlling unit 14 turns the state of the rectangular frame surrounding the cell colony to an original state when the already designated cell colony is designated again by regarding that the designation is released.

After that, the user selects a typical iPS cell colony, and inputs a completion notice to the controlling unit 14 when the designation is completed. Note that FIG. 13A is an enlarged view of the designated cell colony, and FIG. 13B is an enlarged view of the cell colony which is not designated. As it is obvious from FIGS. 13A and 13B, an outline of the designated cell colony is clear, and a distinction from a background is clear, but an outline of the colony which is not designated is not clear, and the distinction from the background is not clear.

Step S73: The controlling unit 14 discriminates whether or not the completion notice is input, the process returns to the step S72 when the completion notice is not input, and transfers to the step S74 when the completion notice is input.

Step S74: The controlling unit 14 writes the frame image displayed when the completion notice is input to the observing data of the focused incubation container 30. Besides, the controlling unit 14 counts the number of the cell colonies designated at the time when the completion notice is input (namely, the number of the rectangular frames of which states are changed at the time when the completion notice is input) as the number of the iPS cell colonies $N_{iPS}$. Besides, the controlling unit 14 counts the number of the cell colonies which are not designated at the time when the completion notice is input (namely, the number of the rectangular frames of which states are not changed at the time when the completion notice is input) as the number of the Non-iPS cell colonies $N_{Non}$. Further, the controlling unit 14 calculates a value of an appearance ratio R of the iPS cell by an expression of "$R=N_{iPS}/(N_{Non}+N_{iPS})$", writes the appearance ratio R to the observing data of the focused incubation container 30, and displays on the monitor 56a.

Step S75: The controlling unit 14 extracts an outline Lc of each of the cell colonies (FIG. 14) by performing outline extracting processing for the binarized colony image I" acquired at the process of the step S71. Note that the outline Lc of the cell colony becomes a closed curve regardless that the cell colony is the iPS cell colony or not. The controlling unit 14 extracts a feature quantity of each cell colony by the following processes (1) to (3).

Figure 15:
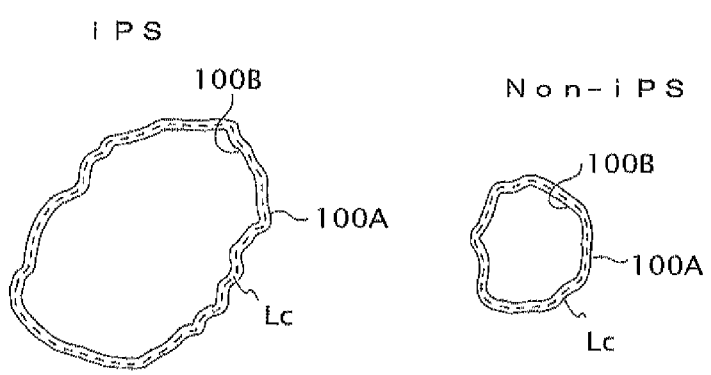
FIG. 15 is a view explaining belt-like areas 100A, 100b.

(1) The controlling unit 14 calculates a belt-like area 100A which is in contact with the outline Lc of the cell colony and positions at an outside of the outline Lc, and calculates a belt-like area 100B which is in contact with the outline Lc and positions at an inside of the outline Lc (FIG. 15).

Figure 16:
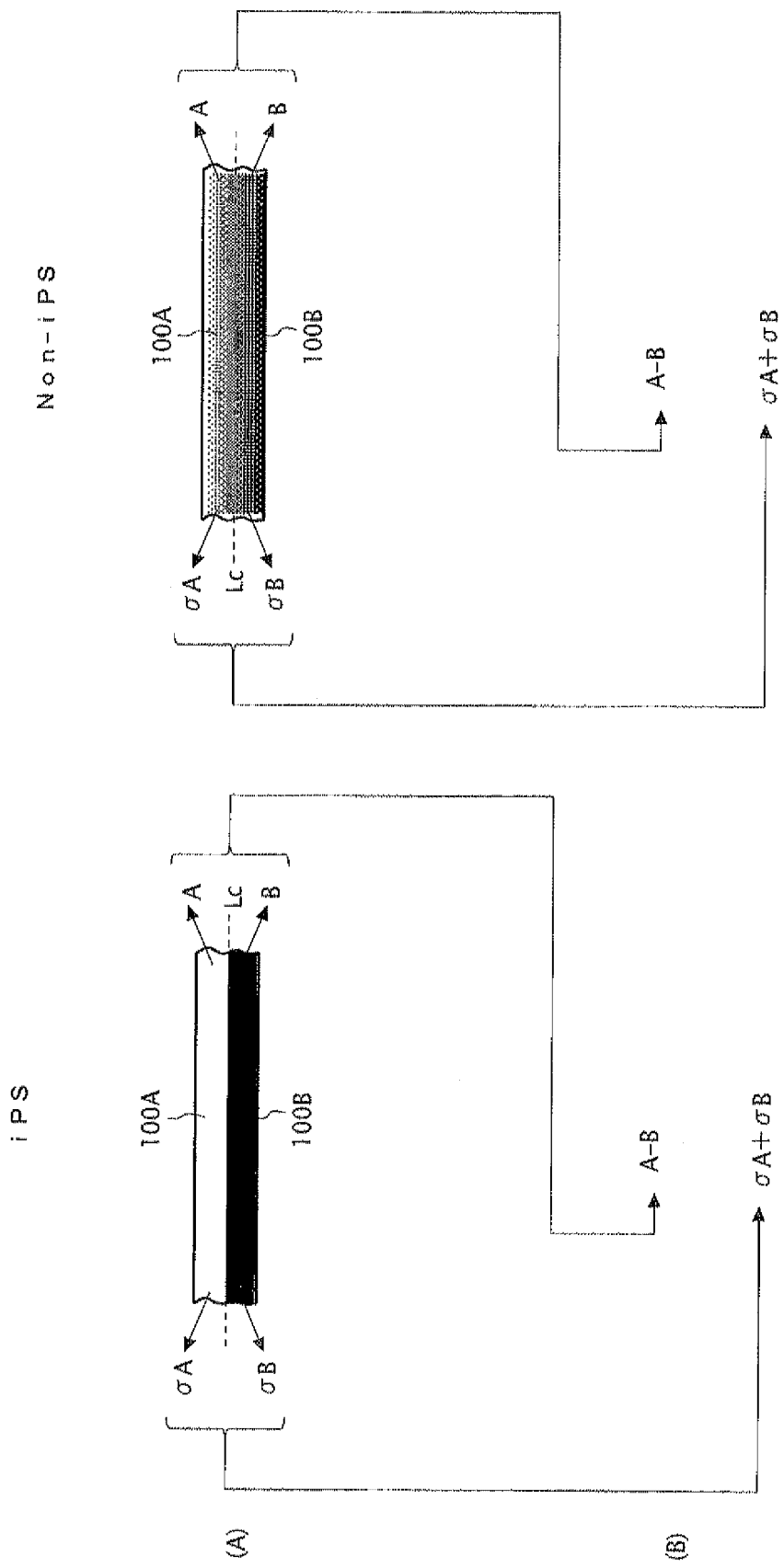
FIG. 16 is a view explaining a feature quantity.

(2) The controlling unit 14 calculates a brightness average value A and a brightness dispersion value σA of a partial phase contrast image corresponding to the belt-like area 100A from among the composite macro image I, and calculates a brightness average value B and a brightness dispersion value σB of a partial phase contrast image corresponding to the belt-like area 100B from among the composite macro image I ((A) of FIG. 16).

(3) The controlling unit 14 calculates a sharpness (A−B) of the outline of the cell colony by subtracting the brightness average value B from the brightness average value A, and calculates roughness (σA+σB) at a periphery of the outline of the cell colony by summing the brightness dispersion value σA and the brightness dispersion value σB ((B) of FIG. 16). The sharpness (A−B) and the roughness (σA+σB) are the feature quantity of the cell colony. Note that the feature quantity having two components is hereinafter referred to as a "feature quantity vector".

Here, as it is schematically illustrated at a left side in FIG. 16, the outline of the iPS cell colony is clear, and brightnesses of the outside and the inside of the outline each are approximately uniform, and therefore, the sharpness (A−B) of the outline of the iPS cell colony is relatively large, and the roughness (σA+σB) at the periphery of the outline of the iPS cell colony is relatively small.

On the other hand, as it is schematically illustrated at a right side of FIG. 16, the outline of the Non-iPS cell colony is not clear, and the brightnesses of the outside and the inside of the outline each are not uniform, and therefore, the sharpness (A−B) of the outline of the Non-iPS cell colony is relatively small, and the roughness (σA+σB) at the periphery of the outline of the Non-iPS cell colony is relatively large.

Figure 17:
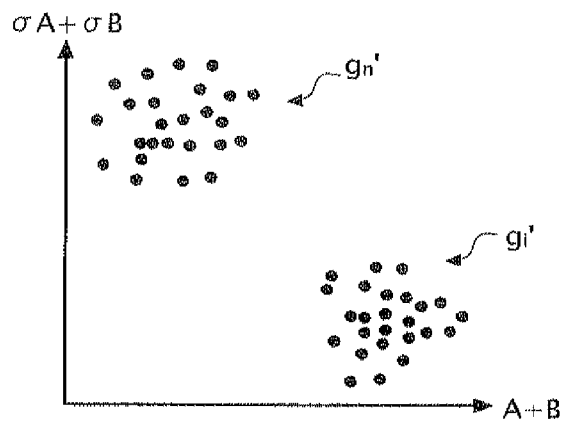
FIG. 17 is a view explaining a learning sample data $g_i{'}$, a leaning sample data $g_n{'}$.
Figure 18:
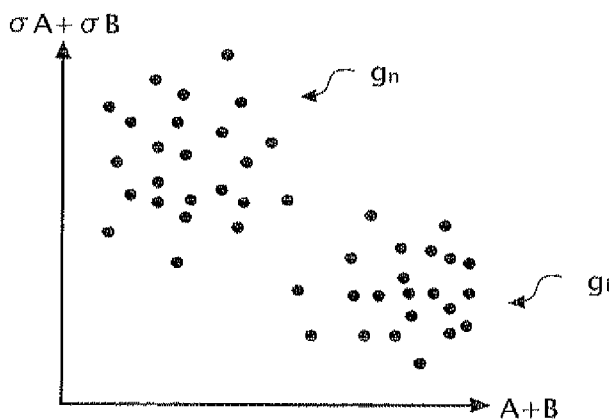
FIG. 18 is a view explaining a learning sample data $g_i$, a leaning sample data $g_n$.
Figure 19:
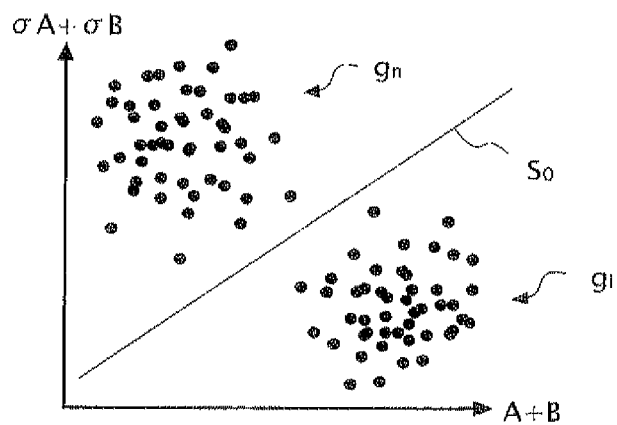
FIG. 19 is a view explaining an updated learning sample data $g_i$, and an updated leaning sample data $g_n$.

Step S76: The controlling unit 14 assumes a vector space of the feature quantity vector (feature quantity space), maps the cell colonies (iPS cell colonies) designated by the user to the feature quantity space in accordance with the feature quantity vector of the cell colonies, and thereby, acquires a set of a map position of the iPS cell colonies (learning sample data $g_i'$). Besides, the controlling unit 14 maps the cell colonies which are not designated by the user (Non-iPS cell colonies) to the feature quantity space in accordance with the feature quantity vector of these cell colonies, and thereby, acquires a set of a map position of the Non-iPS cell colonies (learning sample data $g_n'$) (FIG. 17). The controlling unit 14 sums (sum of sets is taken) the learning sample data $g_i'$ acquired at the present step to the learning sample data $g_i$ of the iPS cell colony at the current time, sums (sum of sets is taken) the learning sample data $g_n'$ acquired at the present step to the learning sample data $g_n$ of the Non-iPS cell colony at the current time, and thereby, updates the learning sample data $g_i$, $g_n$ (FIG. 18 to FIG. 19). Note that the learning sample data $g_i$, $g_n$ when the number of times of experiments is zero (namely, initial values of the learning sample data $g_i$, $g_n$) are zero (empty set).

Further, the controlling unit 14 calculates a hyperplane separating the updated learning sample data $g_i$ and the updated learning sample data $g_n$ as a discriminant plane $S_o$ (FIG. 19). This hyperplane is, for example, a hyperplane in which a distance from the center of gravity of the learning sample data $g_i$ and a distance from the center of gravity of the learning sample data $g_n$ are the same. The controlling unit 14 overwrites a coefficient defining the calculated discriminant plane $S_o$ to a discriminant plane data at the current time to thereby update the discriminant plane data. Note that when it is discriminated whether or not the cell colony is the iPS cell colony by using the discriminant plane $S_o$, the cell colony mapped at an upper side of the discriminant plane $S_o$ is regarded as the Non-iPS cell colony, and the cell colony mapped at a lower side of the discriminant plane $S_o$ is regarded as the iPS cell colony. Note that any of publicly known methods can be used in addition to the method described here as the calculation methods of the discriminant plane $S_o$ in the present step.

Step S77: The controlling unit 14 increments the learning image number data, and finishes the flow of the manual mode.

Next, the operation of the controlling unit 14 in the automatic mode is described.

Figure 7:
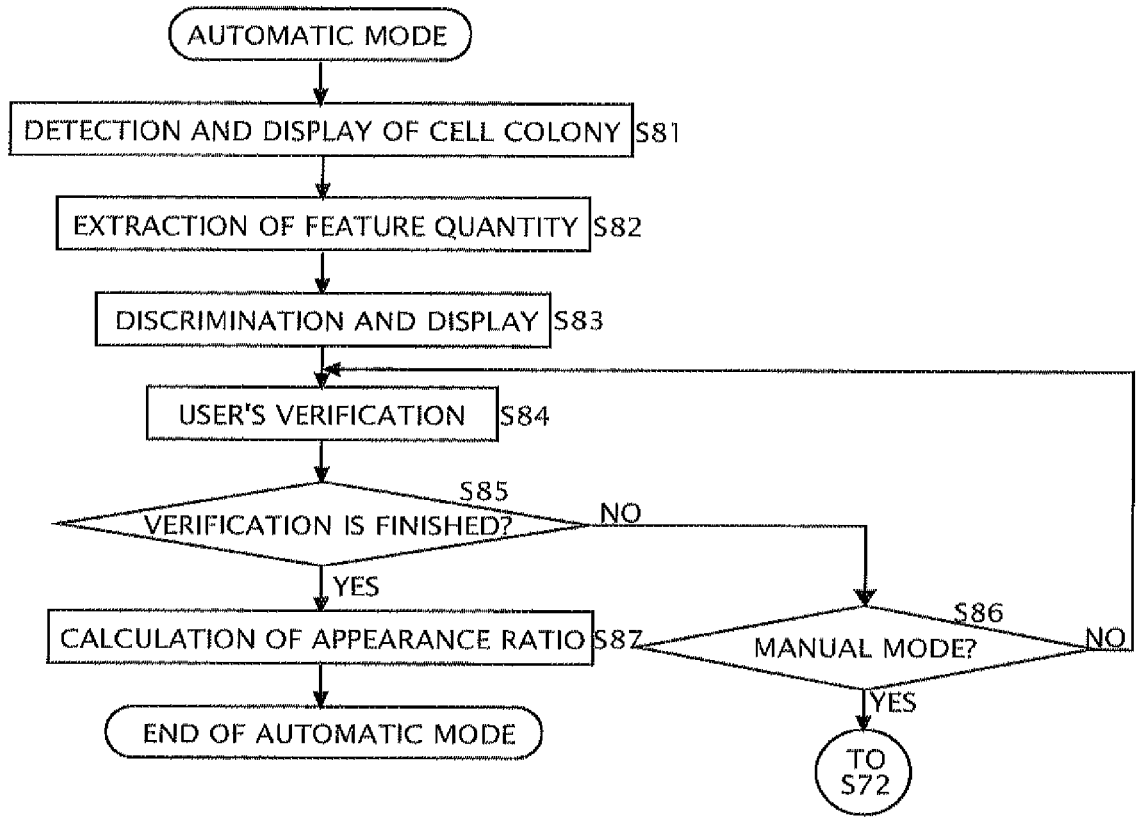
FIG. 7 is an operation flowchart of the controlling unit 14 in an automatic mode.

FIG. 7 is an operation flowchart of the controlling unit 14 in the automatic mode. Hereinafter, each step is described in sequence.

Step S81: The controlling unit 14 provides the composite macro image I (FIG. 8) of the focused incubation container 30 to the image processing part 55 as same as the above-stated step S51, and instructs the image processing part 55 to execute the colony detecting processing. The image processing part 55 acquires the binarized colony image I" (FIG. 10) as same as the above-stated step S71, and outputs the binarized colony image I" as the detection result to the controlling unit 14. The controlling unit 14 regards the respective plural dark areas appeared at the binarized colony image I" as the cell colonies, creates the images of the rectangular frames (frame images) surrounding the respective cell colonies, and overlaps the frame images on the composite macro image I displayed on the monitor 56a (FIG. 11).

Step S82: The controlling unit 14 performs the outline extracting processing for the binarized colony image I" acquired at the process of the step S81 to thereby extract the outline Lc of each of the cell colonies (FIG. 14). The controlling unit 14 extracts the feature quantity vector of each cell colony by the process as same as the above-stated step S75.

Figure 20:
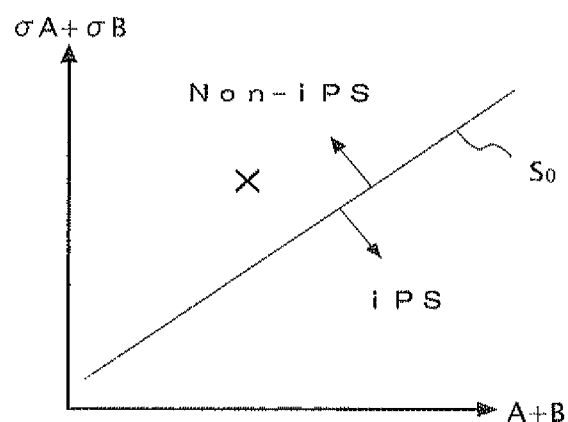
FIG. 20 is a view explaining step S83.

Step S83: The controlling unit 14 sets the discriminant plane $S_o$ at the vector space of the feature quantity vector (feature quantity space) based on the discriminant plane data at the current time (FIG. 20). The controlling unit 14 discriminates whether or not the respective cell colonies extracted at the step S82 are the in cell colonies by the following processes (1) to (3).

(1) The controlling unit 14 maps the cell colony to the feature quantity space in accordance with the feature quantity vector of the cell colony, and thereby, calculates a map position of the cell colony (for example, an "x" mark in FIG. 20).

(2) The controlling unit 14 determines that the cell colony is the Non-iPS cell colony when the map position calculated by the process (1) is at the upper side of the current discriminant plane $S_o$, and determines that the cell colony is the iPS cell colony when the map position calculated by the process (1) is at the lower side of the current discriminant plane $S_o$.

(3) The controlling unit 14 changes a state (for example, color, thickness, line type, and so on) of the rectangular frame surrounding the cell colony on the monitor 56a when the cell colony is determined as the iPS cell colony. The discrimination result by the process (2) is thereby visualized (FIG. 12).

Step S84: The controlling unit 14 instructs the user to verify whether or not the discrimination result of the step S83 is correct. The user verifies whether or not the discrimination result is correct on the monitor 56a, then inputs the completion notice to the controlling unit 14 when the result is correct, and inputs a transfer instruction to the manual mode to the controlling unit 14 when the result is not correct.

Step S85: The controlling unit 14 discriminates whether or not the completion notice is input, then the process transfers to step S86 when the completion notice is not input, and transfers to step S87 when the completion notice is input.

Step S86: The controlling unit 14 discriminates whether or not the transfer instruction to the manual mode is input, and the process returns to the step S84 when the transfer instruction is not input, and transfers to the step S72 in the manual mode when the transfer instruction is input.

Step S87: The controlling unit 14 writes the frame image displayed when the completion notice is input to the observing data of the focused incubation container 30. Besides, the controlling unit 14 counts the number of the cell colonies $N_{iPS}$ which are determined to be the iPS cell colonies at the step S83. Besides, the controlling unit 14 counts the number of the cell colonies $N_{Non}$ which are determined to be the Non-iPS cell colonies at the step S63. Further, the controlling unit 14 calculates a value of the appearance ratio R of the iPS cell by the expression of "$R=N_{iPS}/(N_{Non}+N_{iPS})$", writes the appearance ratio R to the observing data of the focused incubation container 30, displays on the monitor 56a, and finishes the flow of the automatic mode.

As stated above, the controlling unit 14 according to the present embodiment exhibits the automatic mode when the learning image number data exceeds the threshold value (here, 50), and therefore, it is not necessary for the user to designate the iPS cell colony in the experiment at a second time or later when the number of the incubation containers 30 used in the first experiment is 50 pieces.

Besides, the controlling unit 14 according to the present embodiment extracts the feature quantity vector representing clarity of the outline part of the cell colony from the composite macro image I being the phase contrast microscope image, and automatically discriminates whether or not the cell colony is the iPS cell colony based on the feature quantity vector and the discriminant plane $S_o$ set at the feature quantity space in the automatic mode, and therefore, it is not necessary to introduce the marker gene to the cell in advance.

Besides, the controlling unit 14 according to the present embodiment extracts a difference (A−B) of the brightness average value A of the belt-like area 100A positioning at the outside of the outline Lc of the cell colony and the brightness average value B of the belt-like area 100B positioning at the inside of the outline Lc as one component of the feature quantity vector, and therefore, it is possible to perform the discrimination whether or not the cell colony is the iPS cell colony with high accuracy.

Besides, the controlling unit 14 according to the present embodiment extracts the sum (σA+σB) of the brightness dispersion value σA of the belt-like area 100A and the brightness dispersion value σB of the belt-like area 100B as one component of the feature quantity vector, and therefore, it is possible to perform the discrimination whether or not the cell colony is the iPS cell colony with high accuracy.

Besides, the controlling unit 14 according to the present embodiment sets the discriminant plane $S_o$ being a discriminant criterion of the automatic discrimination based on the result of the manual discrimination (teaching) of the user for the plural composite macro images I, and therefore, it is possible for the user to customize the incubator 11 by himself/herself.

Besides, the controlling unit 14 according to the present embodiment exhibits the automatic mode only after the learning image number data exceeds the threshold value (here, 50), and therefore, it is possible to surely make the accuracy of the automatic discrimination to a certain level or more.

Besides, the controlling unit 14 according to the present embodiment immediately starts the manual discrimination (teaching) when the user has dissatisfaction with the discrimination result of the automatic discrimination, and therefore, it is possible to avoid a possibility of an error measurement.

Besides, in the controlling unit 14 according to the present embodiment, it is possible to perform the manual discrimination (teaching) over and over in accordance with the request from the user even when the learning image number data exceeds the threshold value (here, 50), and therefore, it is possible for the user to enhance the accuracy of the automatic discrimination according to need.

Note that the operation of the controlling unit 14 illustrated in FIG. 5 can be modified as follows.

Namely, the steps S6, S7 in FIG. 5 are not performed and the step S8 (a subroutine process in FIG. 7) is inserted between the steps S5, S9. However, in this case, the controlling unit 14 executes the teaching process (the subroutine process in FIG. 6) acquiring the learning sample data of the iPS cell colony in advance.

The controlling unit 14 in the teaching process lets the user designate the iPS cell colony on the composite macro image I (the number of designation is arbitrary), and the process illustrated in the steps S74 to S77 in FIG. 6 (manual mode) are preformed, and thereby, acquires and stores the learning sample data of the iPS cell colony.

Accordingly, the controlling unit 14 in the later step is able to perform the automatic discrimination process automatically discriminating the iPS cell colony from the composite macro image I being a detection object based on the stored learning sample data. As stated above, the teaching process is performed separately, and thereby, it is possible to immediately start the automatic discrimination process at an arbitrary timing.

Note that it is possible to store the learning sample data to the other apparatus of the same model as the present apparatus, and in this case, it is possible to omit the teaching process at the apparatus.

Besides, the controlling unit 14 according to the present embodiment may use another index representing a brightness gradient from the inside to the outside of the outline though the value (A−B) is used as an index of the sharpness of the outline. For example, a value (B/A) may be used.

Besides, the controlling unit 14 according to the present embodiment uses the sum (σA+σB) of the brightness dispersion value σA of the belt-like area 100A and the brightness dispersion value σB of the belt-like area 100B as an index of the roughness at the periphery of the outline, but a sum (ΔA+ΔB) of a brightness difference ΔA of the belt-like area 100A and a brightness difference ΔB of the belt-like area 100B may be used. Note that the "brightness difference of the belt-like area" described here indicates a difference between a maximum brightness and a minimum brightness of the partial phase contrast image corresponding to the belt-like area.

Besides, the controlling unit 14 according to the present embodiment uses a two-dimensional feature quantity vector as the feature quantity vector, but a one-dimensional or three or more dimensional feature quantity vector may be used.

Besides, the controlling unit 14 according to the present embodiment sets the components of the feature quantity vector as the combination of the sharpness of the outline and the roughness at the periphery of the outline, but it may be the other combinations. An area size inside the outline, the brightness average value of the area inside the outline, and so on can be cited as quantities effective as the components of the feature quantity vector in addition to the sharpness of the outline and the roughness at the periphery of the outline.

Besides, in the present embodiment, the feature quantity extracted from the phase contrast microscope image of the cell colony is set to be the feature quantity representing the clarity of the outline of the cell colony, but it may be set to be the feature quantity representing a degree of change of an edge of the cell colony (specifically, an amount of change of an edge signal). The amount of change of the edge signal can be extracted by differential processing and so on for the phase contrast microscope image of the cell colony. For example, edge detection processing by means of a differentiation (the differential processing extracting a part in which the edge signal changes is used), edge detection processing by means of Laplacian (Laplacian using quadratic differential as a method detecting only a strength of edge is used), and so on.

Besides, in the incubator according to the present embodiment, a part or all of the operation of the image processing part 55 may be performed by the controlling unit 14. Besides, a part or all of the operation of the controlling unit 14 may be performed by the image processing part 55.

Besides, in the present embodiment, the incubation object is the human somatic cells, but it may be the somatic cells of the other animals. However, there is a possibility in which the discriminant criterion whether or not the cell is the iPS cell colony may be different depending on kinds of the animals, and therefore, the controlling unit 14 may prepare the above-stated learning image number data, the learning sample data, the discriminant plane data by each kind of each animal.

The many features and advantages of the embodiments are apparent from the detailed specification and, thus, it is intended by the appended claims to cover all such features and advantages of the embodiment that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. An image processing apparatus, comprising:
    an outline extracting processing device configured to input a phase contrast image of a cell colony acquired by an observing device, and extract an outline of the cell colony,
    an extracting device configured to set, along the outline, a belt-like area with a predetermined width including the outline of the cell colony, the predetermined width of the belt-like area being defined by an outer belt line and an inner belt line, the outline being disposed between the outer belt line and the inner belt line and being spaced from the outer belt line and the inner belt line,
    the extracting device being further configured to extract a feature quantity of the outline of the cell colony based on a combination of brightness information of an inner area between the outline and the inner belt line and brightness information of an outer area between the outline and the outer belt line, and
    an automatic discriminating device configured to automatically discriminate whether or not the cell colony is an iPS cell colony based on a discriminant criterion determined in advance and the feature quantity extracted by the extracting device.

2. The image processing apparatus according to claim 1, wherein
    the extracting device extracts a sharpness of the outline of the cell colony as the feature quantity of the outline of the cell colony.

3. The image processing apparatus according to claim 1, wherein
    the extracting device extracts a roughness of the outline of the cell colony as the feature quantity of the outline of the cell colony.

4. The image processing apparatus according to claim 1, wherein
    the brightness information corresponds to statistical information of brightness of the belt-like area.

5. The image processing apparatus according to claim 1, wherein
    the extracting device extracts a degree of change of an edge of the cell colony as the feature quantity of the outline of the cell colony.

6. The image processing apparatus according to claim 2, wherein
    the extracting device extracts the sharpness of the outline of the cell colony based on a brightness average value of the outer area and a brightness average value of the inner area, or extracts based on a brightness gradient from the inner area to the outer area.

7. The image processing apparatus according to claim 3, wherein
    the extracting device extracts the roughness of the outline of the cell colony based on a brightness dispersion value of the outer area and a brightness dispersion value of the inner area, or extracts based on a brightness difference (a difference between a maximum brightness and a minimum brightness) of the outer area and a brightness difference (a difference between a maximum brightness and a minimum brightness) of the inner area.

8. The image processing apparatus according to claim 1, wherein
    the extracting device uses at least one of a brightness dispersion value and a brightness average value of the belt-like area as the brightness information.

9. The image processing apparatus according to claim 8, wherein
    the extracting device extracts a difference between the brightness average value of the outer area and the brightness average value of the inner area as at least one component of the feature quantity.

10. The image processing apparatus according to claim 8, wherein
    the extracting device extracts a sum of the brightness dispersion value of the outer area and the brightness dispersion value of the inner area as at least one component of the feature quantity.

11. The image processing apparatus according to claim 1, further comprising:
    a teaching device configured to display a phase contrast image of a plurality of cell colonies on a monitor, and configured to let an operator perform a manual discrimination whether or not the cell colony is the iPS cell colony as for each of the cell colonies,
    an extracting device configured to extract a feature quantity of the outline as for each of the cell colonies, and
    a setting device configured to set a discriminant criterion of the automatic discriminating device based on the feature quantity extracted as for each of the cell colonies by the extracting device and a result of the manual discrimination performed by the operator as for each of the cell colonies.

12. An incubation observing apparatus, comprising:
    a temperature-controlled room housing an incubation container;
    an imaging device acquiring a phase contrast image of the incubation container housed in the temperature-controlled room; and
    the image processing apparatus according to claim 1 processing the phase contrast image acquired by the imaging device.

13. An image processing method, comprising:
    an outline extracting processing step inputting a phase contrast image of a cell colony acquired by an observing device, and extracting an outline of the cell colony;

an extracting step including setting, along the outline, a belt-like area with a predetermined width including the outline of the cell colony, the predetermined width of the belt-like area being defined by an outer belt line and an inner belt line, the outline being disposed between the outer belt line and the inner belt line and being spaced from the outer belt line and the inner belt line, the extracting step further including extracting a feature quantity of the outline of the cell colony based on a combination of brightness information of an inner area between the outline and the inner belt line and brightness information of an outer area between the outline and the outer belt line; and an automatic discriminating step automatically discriminating whether or not the cell colony is an iPS cell colony based on a discriminant criterion determined in advance and the feature quantity extracted at the extracting step.

* * * * *